(12) United States Patent
McKinnon et al.

(10) Patent No.: US 7,090,646 B2
(45) Date of Patent: Aug. 15, 2006

(54) PLUNGER-LESS SYRINGE FOR CONTROLLING BLOOD FLOW

(75) Inventors: Robert J. McKinnon, Highlands Ranch, CO (US); Dean H. Iwasaki, Denver, CO (US)

(73) Assignee: Westmed, Inc., Englewood, CO (US)

( * ) Notice: Subject to any disclaimer, the term of this patent is extended or adjusted under 35 U.S.C. 154(b) by 324 days.

(21) Appl. No.: 10/658,890

(22) Filed: Sep. 9, 2003

(65) Prior Publication Data

US 2005/0054949 A1    Mar. 10, 2005

(51) Int. Cl.
*A61B 5/00*    (2006.01)
*B65D 81/00*    (2006.01)

(52) U.S. Cl. ...................................... 600/576

(58) Field of Classification Search ............. 600/573, 600/576, 578, 565; 604/88, 187, 191, 218, 604/220, 246, 196, 203; 206/366, 365
See application file for complete search history.

(56) References Cited

U.S. PATENT DOCUMENTS

| 4,133,304 A | | 1/1979 | Bailey ........................... 128/2 |
| 4,393,882 A | | 7/1983 | White ......................... 128/764 |
| 4,542,749 A | * | 9/1985 | Caselgrandi et al. ........ 600/565 |
| 4,753,345 A | * | 6/1988 | Goodsir et al. ............. 206/366 |
| 5,032,117 A | * | 7/1991 | Motta .......................... 604/88 |

* cited by examiner

*Primary Examiner*—Max Hindenburg
*Assistant Examiner*—Brian Szmal
(74) *Attorney, Agent, or Firm*—Sheridan Ross P.C.

(57) ABSTRACT

A plunger-less syringe and method of use are disclosed. The syringe includes an outer housing fixedly attached to an interior receptacle for receiving a quantity of blood. The syringe has a vent that allows air to escape from the receptacle as blood flows therein. The vent can include a filter for use in preventing blood from exiting the interior receptacle. A vent cap is provided having a recess for mating with a syringe having a plunger, wherein blood flow into the receptacle can be controlled. A plurality of the plunger-less syringes can be packaged in a container, wherein the blood pathway of the syringes is sterilized and without having any exterior sterile packaging.

18 Claims, 4 Drawing Sheets

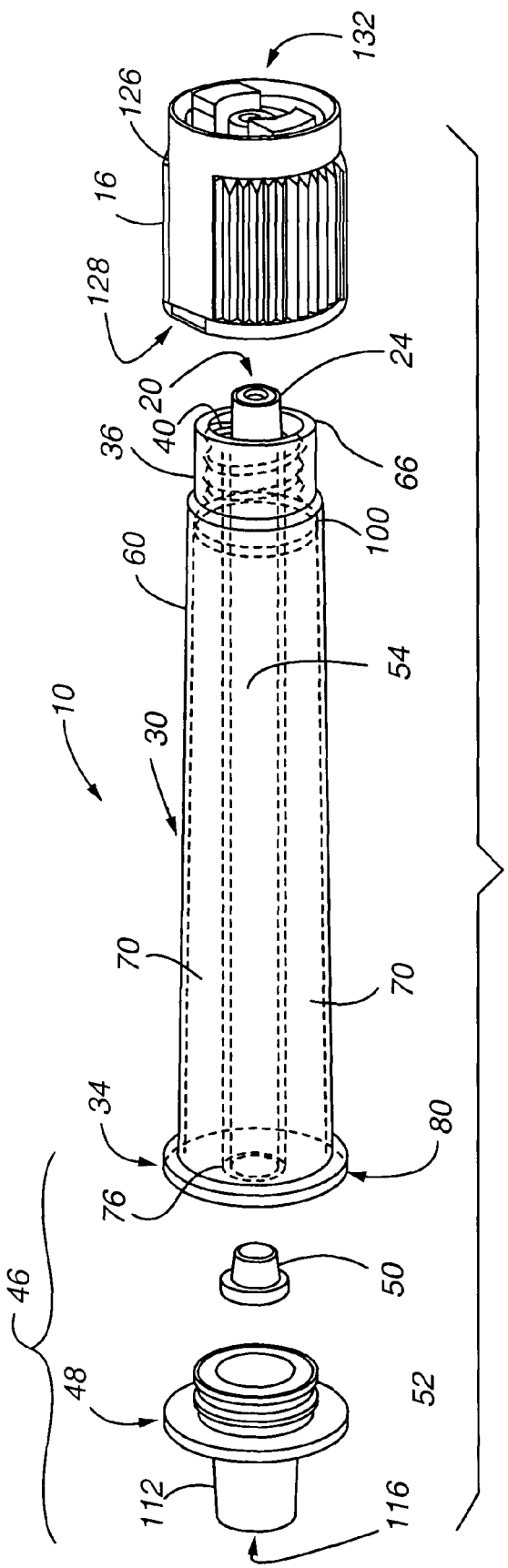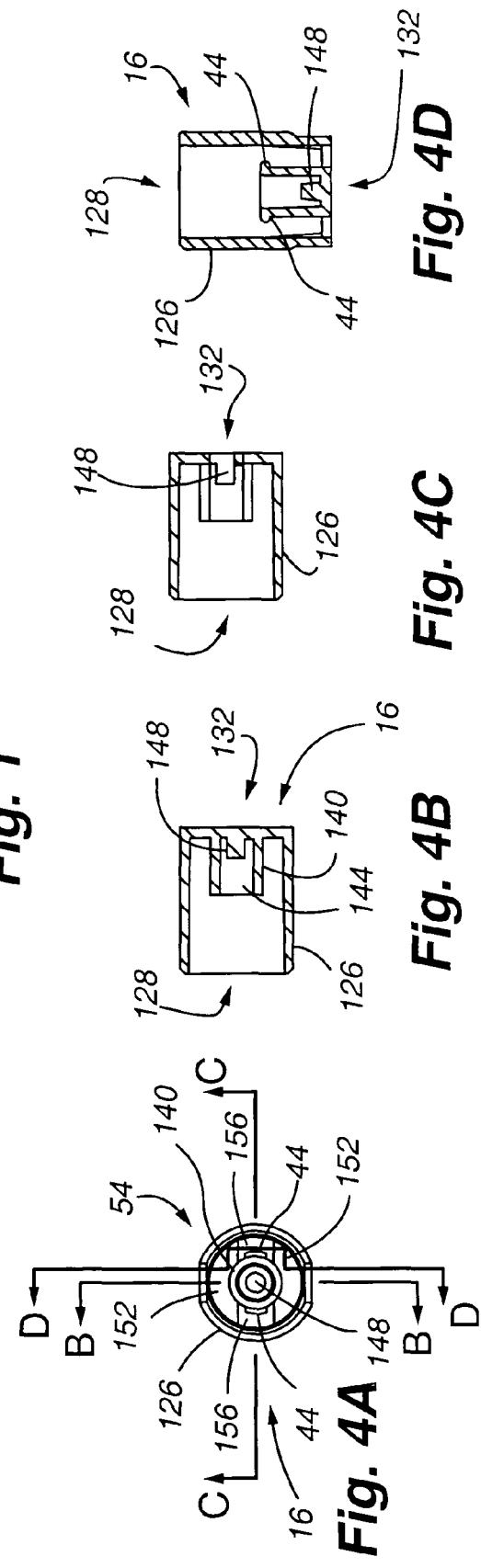

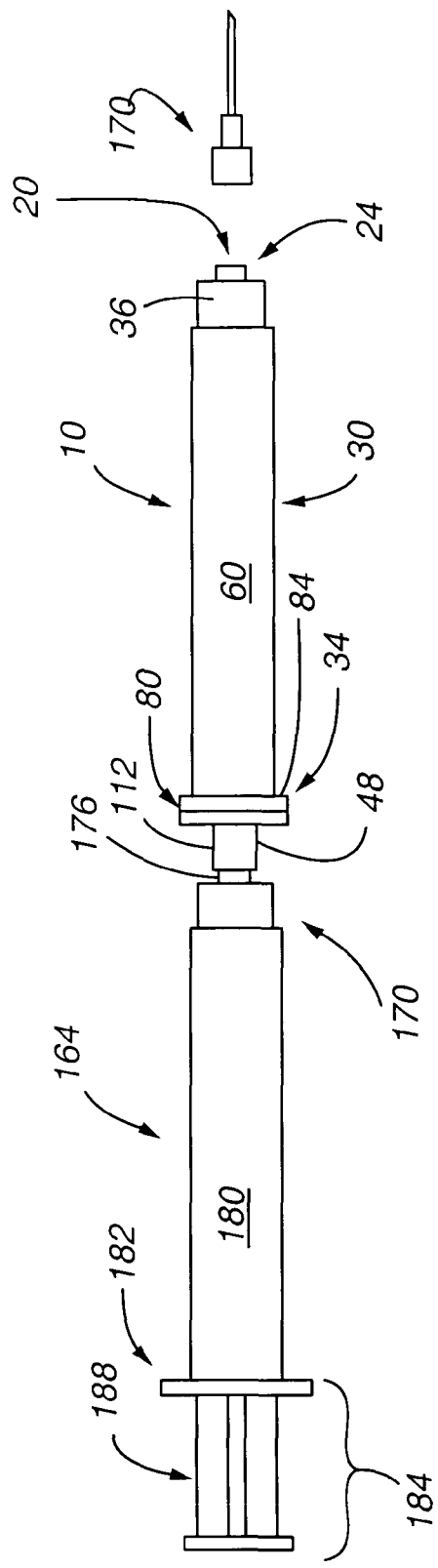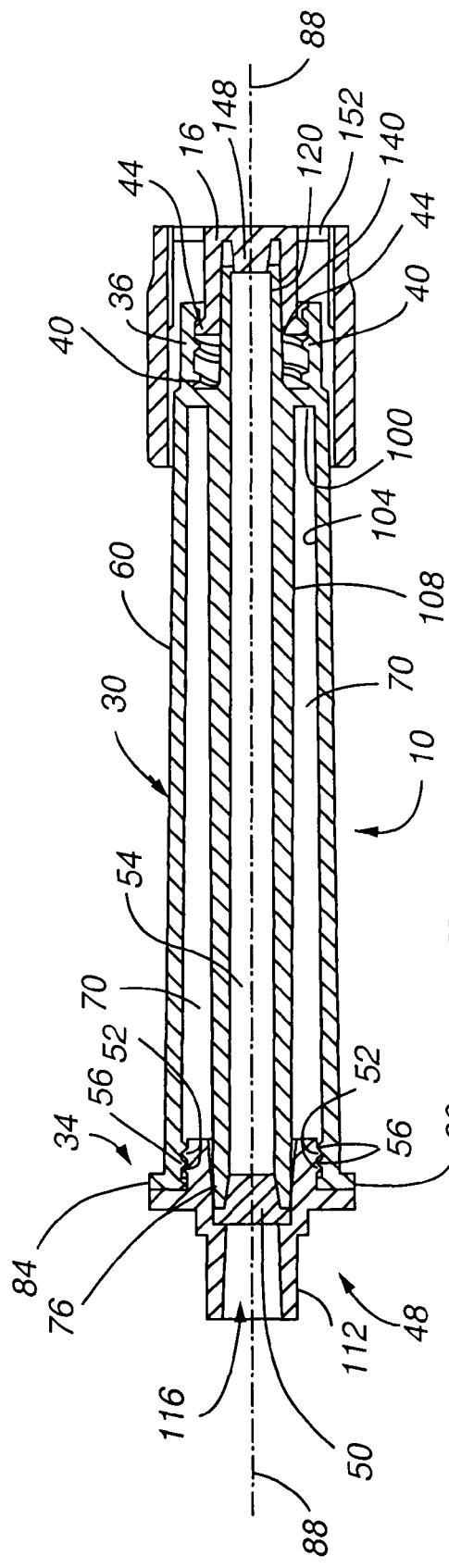

PLUNGER-LESS SYRINGE FOR CONTROLLING BLOOD FLOW

FIELD OF THE INVENTION

The present invention relates to a plunger-less syringe for receiving blood, and in particular, to such a syringe including an outer housing having first dimensions an interior blood collection receptacle fixedly attached thereto, wherein the blood collection receptacle maybe of substantially reduced volume, and wherein a plunger-type syringe may be operably attached to the plunger-less syringe when assistance is needed in drawing a patient's blood.

BACKGROUND OF THE INVENTION

There are numerous syringes available for drawing a patient's blood. Many syringes have a movable plunger for assisting in the drawing of blood and/or exiting blood from such a syringe. However, there are also syringes that are plunger-less syringes that collect blood by relying on the pressure of the blood within a vein or artery to fill a receptacle such as a capillary tube such as U.S. Pat. No. 4,393,882 filed Nov. 17, 1980. Accordingly, some such plunger-less syringes have an opening to the interior of the blood collecting receptacle that is opposite to where the blood enters the receptacle so that air within the receptacle exits as the blood enters. This has the advantage of allowing the air to escape so that there is no air pressure build up in the receptacle that could inhibit the flow of blood into the receptacle. However, air may remain in contact with the drawn blood which can compromise blood analysis assays, such as the determination of $O_2$ in the blood collected blood.

It is also known and if all the air can be expelled from the receptacle, then a more accurate blood analysis can be performed regarding such gases as $O_2$ that otherwise might diffuse out of the collected blood.

In order to reduce or eliminate air contact with the collected blood, various techniques are known for closing air exit openings in the blood collection receptacles of plunger-less syringes. In one technique, a filter is provided in the air exit opening such that the filter allows air to escape until blood commences to saturate the filter, but after the filter is saturated, it blocks both blood and air from entering and exiting the blood collection receptacle via the opening. In a second technique disclosed in U.S. Pat. No. 4,133,304 (i.e., the '304 patent), an elastomeric seal is provided in the air exit opening, wherein the seal includes a sealable orifice having a retaining element therein (e.g., a thread of a fibrous material). Air and/or blood are able to exit, via the orifice, out of the blood collection receptacle (denoted a "capillary tube" in the '304 patent) until the retaining element is removed from the orifice causing the orifice to close and thereby preventing further contact between the collected blood and the air external to the receptacle. However, the syringes of the '304 patent require assembly wherein, e.g., the capillary tube is fitted within an exterior housing. Moreover, the fitting is only a frictional fitting provided at the needle attaching end of the housing; thus, the receptacle and housing are not designed to remain attached to one another during extensive handling and/or storage. But separation and removal of the capillary tube from the housing has drawbacks in that for the plunger-less embodiment disclosed: (a) during separation, the opening for receiving the drawn blood is apparently unsealed, and presumably remains unsealed until an extra step of resealing is performed, and (b) since the quantity of blood drawn may be small (particularly from infants), such capillary tubes are typically, as their name implies, thin and accordingly not conducive to direct user handling.

Thus, it would be desirable to have a plunger-less syringe wherein: (a) substantially all the air in the blood collection receptacle is expelled as blood is being collected, (b) there is a reduced amount of assembly and/or disassembly immediately prior to and/or after use, and (c) the syringe has an exterior housing that is sized for ease of user handling while the blood collection receptacle therein is sized to accept only the volume of blood needed, and wherein the exterior housing and the receptacle are suitably secured together so that the entire syringe can be handled and/or stored with collected blood therein.

Additionally, note that although plunger-less syringes can be less expensive to produce than syringes with plungers, and can be substantially smaller, plunger-less syringes typically have no means for controlling the movement of blood into or out of their blood collection receptacles. Thus, e.g., in cases where arterial blood is being drawn and there is insufficient blood pressure to draw the blood, alternative blood drawing syringes may be used, or specially designed additional components may be required (as is disclosed in the '304 patent discussed above). Accordingly, it would be also desirable to have plunger-less syringe, wherein a conventional plunger type syringe could be attached thereto for assisting in the withdrawing of a patient's blood.

SUMMARY OF THE INVENTION

The present invention is a method and apparatus for obtaining blood from a patient, storing the blood obtained, and/or providing the obtained blood to a blood analysis instrument. In particular, the invention includes a novel plunger-less syringe, particularly suited for collecting arterial blood, that can include an outer housing or tube with dimensions of a conventional 3 cc syringe, and an interior reduced size receptacle or tube for receiving and collecting blood. That is, the interior receptacle may be substantially smaller than the outer housing. The blood collected can be less than about a 400 microliter volume and can be obtained in less than about three seconds at normal adult pressures. Additionally, the novel syringe includes, in one embodiment, at the end (i.e., a "proximal end") of the syringe opposite from the end (i.e., a "distal end") of the syringe where blood enters the interior receptacle, a vent that allows air to escape from the interior receptacle as blood flows into the receptacle (and also may allow air to enter into the interior receptacle when blood is urged out of this receptacle and into, e.g., a blood analysis instrument). Thus, it is an aspect of the invention that blood can entirely fill the interior receptacle and completely displace the air therein so that no unwanted air (e.g., an amount of air that would detrimentally affect the analysis of the blood sample being collected) remains within this receptacle. Moreover, it is an aspect of the invention that the vent includes a filter which may be a hydrophobic filter for preventing blood from exiting the interior receptacle at the vent. Covering the vent, at the proximal end, is a vent cap that includes a mating portion having a recess for mating with a conventional 3 cc hypodermic syringe having a plunger therein. In particular, the needle attachment end (i.e., the distal end) of a conventional syringe design mates with this recess for providing an gas flow path between the interior of the conventional plunger-type syringe and the plunger-less syringe of the present invention. Moreover, the gas flow path is through the filter of the vent. Thus, since the syringe of the present invention does not include a plunger for withdrawing blood from a patient or urging blood to exit the interior receptacle, in those cases where additional force is desirable for assisting in the entry to or exit from the syringe of the invention, such a conventional syringe having a plunger can be operably attached to the vent cap to thereby create such a force. In causing exiting of blood, sufficient force can be generated to overcome the filter so that air can act as a driving force behind the column of blood to move the blood. Once adapted for blood sample aspiration, the present invention can also be used to obtain "cord gases."

It is also an aspect of the present invention to include methods for utilization of the novel plunger-less syringe for drawing blood, holding blood therein, and providing blood to, e.g., a blood analysis instrument. In particular, the present invention includes methods for utilizing the plunger-less syringe for drawing blood with and without the assistance of a conventional plunger-type syringe as described above.

It is yet a further aspect of the present invention to provide a plurality of the plunger-less syringes in a container for distribution, wherein the individual syringes therein are not individually wrapped or packaged, and wherein the container is appropriately constructed so that it can be sterilized (e.g., E-beam) with the syringes remaining in the container.

Other features and benefits of the present invention will become evident from the description hereinbelow together with the accompanying drawings.

BRIEF DESCRIPTION OF THE DRAWINGS

FIG. 1 shows an exploded perspective view of a capped syringe 160 of the present invention, including the novel plunger-less syringe 10 and a locking cap 16 for securing to the distal end 24 of the syringe 10 that is adjacent to the locking cap in the present figure.

FIG. 2 shows a cross section of the syringe 10 with the locking cap 16 secured thereto.

FIG. 3 shows the syringe 10 of the present invention operably connected to a syringe 164 having a plunger 184 for drawing blood into the syringe 10 or expelling blood from the syringe 10.

FIGS. 4A–4D show various views of the locking cap 16. In particular, FIG. 4A shows the locking cap 16 from its end 128 (FIG. 1). FIGS. 4B–4D show various cross sections of the locking cap 16, wherein FIG. 4B is the cross section defined by the sectioning plane and view directions corresponding to the arrows B of FIG. 4A; FIG. 4C is the cross section defined by the sectioning planes and view directions corresponding to the arrows C of FIG. 4A; and FIG. 4D is the cross section defined by the sectioning plane and view directions corresponding to the arrows D of FIG. 4A.

DETAILED DESCRIPTION OF THE DRAWINGS

Figure 5:
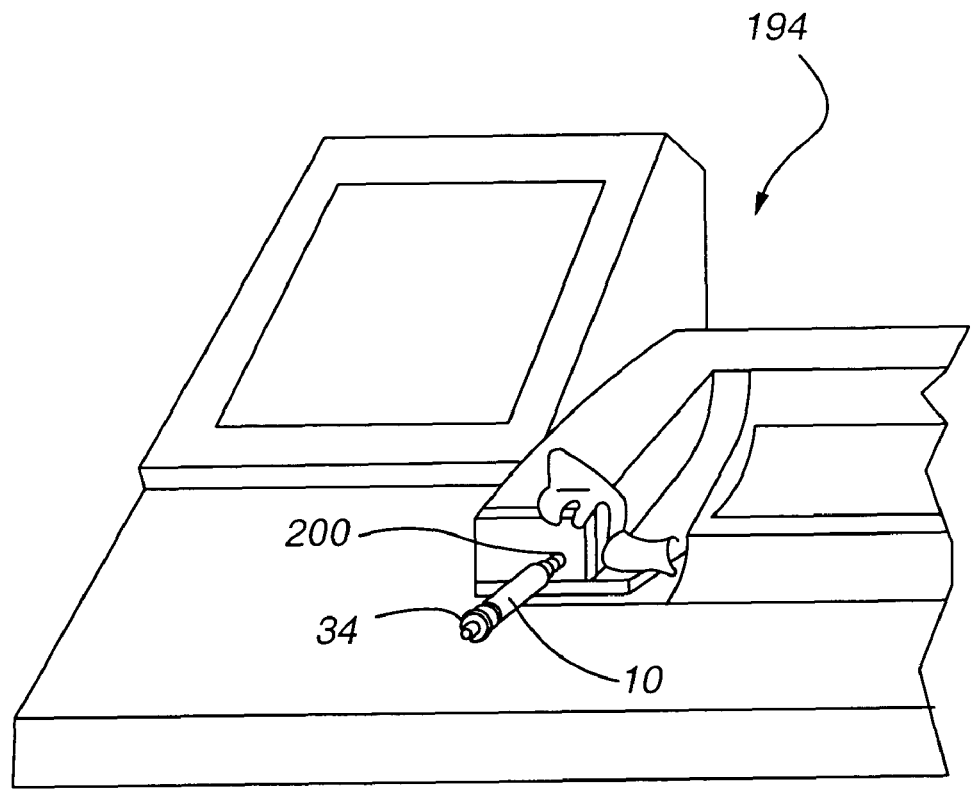
FIG. 5 shows one embodiment of how a syringe 10 of the present invention can be connected to a blood analysis instrument 194 for receiving blood from the syringe 10.

Referring to FIG. 1, a blood receiving syringe 10 provided by the present invention is shown together with a sealing cap or the locking cap 16 which is used to (re)seal the opening 20 in the distal end 24 of the syringe 10 when the syringe is, e.g., not being used to draw blood. Thus, the locking cap 16 is preferably provided over the opening 20 when a hypodermic needle assembly (not shown in FIG. 1) is not attached to the distal end 24 for drawing blood through the opening 20. The syringe 10 includes a body portion 30 (denoted merely "body 30" hereinbelow) whose exterior is generally cylindrical. The body 30 extends from the distal end 24 (which is the distal end of both the syringe 10 and the body 30) to a body proximal end 34. The body 30 may be a single unitary component made of a plastic. Moreover, the body 30 can be manufactured by, e.g., injection molding techniques, since there are no enclosed voids within the body 30 (as will evident from the description below). In one embodiment, the distal end 24 of the body 30 includes a cylindrical cap fitting 36 having threads 40 provided on the interior surface, wherein tabs 44 (FIGS. 4A and 4D) within the locking cap 16 mate with the threads 40 for securing the cap 16 to the body 30. At the proximal end 46 (FIG. 1) of the syringe 10, the syringe 10 includes a vent cap 48 which, in one embodiment, is made of a resilient material such as polypropylene. The vent cap 48 includes ridges 52 that contact ridges 56 (FIG. 2) within an interior of the body proximal end 34 to thereby secure the vent cap 38 to the body proximal end. Secured between the vent cap 38 and the body proximal end 34, the syringe 10 includes a vent 50 that allows air to escape from a blood collection receptacle 54 (FIG. 2) as blood flows therein, and also prevents blood from flowing through the vent. Such vents are well known in the art, and include hydrophobic filters which allow the passage of air through such a filter until blood completely contacts or saturates the filter, at which time neither blood nor air can cross the hydrophobic filter. A description of hydrophobic filters for venting a syringe is disclosed in, e.g. U.S. Pat. No. 4,572,210 filed Mar. 18, 1982, this reference being fully incorporated herein by reference. Note that references herein to the proximal end 46 of the syringe 10 is intended to denote at least the vent cap 38 and the body proximal end 34.

The receptacle 54, provided within syringe 10, may be substantially cylindrical and extend from the proximal end 46 to the distal end 24 wherein the opening 20 opens to the interior of the receptacle. Accordingly, the receptacle extends through the cylindrical cap fitting 36 whose interior threaded surface is spaced apart from and faces the portion of the receptacle 54 that extends through an interior of the cap fitting. Note that the distal end (FIGS. 1 and 3) of the receptacle 44 is identical with the distal end 24 of the syringe 10.

Referring to both FIGS. 1 and 2, the body 30 includes an inner tubular member which is the receptacle 54 referenced above, and an outer housing member 60 which surrounds the receptacle 54 substantially along its entire length. In particular, the outer housing member 60 extends from the body proximal end 34 to the circular end 66 (of the cap fitting 36) from which the distal end 24 protrudes. The outer housing member 60 is spaced apart from the receptacle 54 by an annular space 70. At the body proximal end 34, the annular space 70 is sealed by the vent cap 48, and the proximal end 76 of the receptacle 54 extends a small distance (e.g., approximately 0.06 cm) further beyond a proximal end 80 of the outer housing member 60. Note that the proximal end 80 includes an annular rim 84 that extends outwardly from a longitudinal central axis 88 (FIG. 2) of the syringe 10. Further note that the annular space 70 is sized so that the outside diameter of the syringe 10 is effectively identical to that of a conventional 3 cc syringe. Thus, it is an aspect of the present invention that the receptacle 54 can vary in size and in the quantity of blood it can retain depending on the dimensions of the annular space 70. In one embodiment, the blood retaining volume of the receptacle 54 may be approximately 0.17 cubic centimeters (cc). However, other smaller or larger blood retaining volumes are within the scope of the invention. In one embodiment, if the annular space 70 were eliminated, the blood retaining volume for the syringe 10 of FIGS. 1 and 2 would be approximately 1.91 cc.

The syringe 10 further includes an annular connection or bridge 100 between the interior wall 104 of the outer housing member 60 and exterior wall 108 of the receptacle 54, wherein the bridge 100 secures the outer housing member and the receptacle together. In the embodiment shown in FIGS. 1 and 2, the bridge 100 has an annular shape traversing the space between the interior wall 104 and the exterior wall 108 and thereby sealing the more distal end of the annular space 70. Accordingly, the bridge 100 is substantially adjacent to the cylindrical cap fitting 36. However, other embodiments of the bridge 100 are also within the scope of the present invention. For example, the bridge 100 need not fully seal the more distal end of the annular space 70. Instead, the bridge 100 may, e.g., include a plurality of spokes (not shown) that: (i) relative to the axis 88, radially span the distance between the interior wall 104 and the exterior wall 108, and (ii) are distributed in a manner that will effectively secure the outer housing member 60 to the receptacle 54. In particular, two, three or four such spokes may provided in various embodiments of the syringe 10. Moreover, at least portions of the bridge 100 may be located further toward the proximal end 76 of the receptacle 54 than shown in FIGS. 1 and 2. For example, two opposing spokes of such a bridge 100 may be located within the annular volume filled by the bridge 100 shown in FIGS. 1 and 2, and another two opposing such spokes may be located more toward the proximal end 76 of the receptacle. Additionally, note that the bridge 100 may be integrally formed in the syringe 10 wherein the syringe is formed as a singly unitary piece; e.g., via an a plastic injection molding technique.

The vent cap 48 is secured to the body proximal end 34 for sealing the annular space 70, and for both covering and securing the vent 50 within the proximal end 76 of the receptacle 54. The vent cap 48 includes an extension 112 which includes a passageway 116 therein. When operably attached to the body 30, the passageway 116 is in air communication with the vent 50 so that, e.g., air is able to escape the receptacle 54 effectively only through the vent 50 and this passageway. Note that in one embodiment, the vent cap 48 is molded from polypropylene.

Alternative embodiments of the vent cap 48 and/or the vent 50 are also within the scope of the invention. In particular, the vent 50 can be secured within the vent cap 48 (e.g., in the passageway 116). Thus, a "vent" subassembly including the vent cap 48 with its vent 50 could be assembled separated from the rest of the syringe 10. Such an embodiment, the vent subassembly be the considered as the vent for the present invention.

For describing the locking cap 16, reference is made to FIGS. 1, 2, and 4A through 4D. The locking cap 16 has a generally cylindrical exterior 126, and the ends 128 and 132 thereof have openings that allow air to pass through the locking cap from each of these ends to the other. The end 128 provides access to a substantially cylindrical interior with a central cylinder 140 (FIGS. 4A and 4B) therein. The central cylinder 140 has an interior 144 that is open at its end nearest the end 128. Centrally located at the opposite end the of interior 144 is a plug 148 for plugging the opening 20 when the locking cap 16 is operably attached to the syringe 10. Note that the cylinder 140 is attached to the cylindrical exterior 126 by semi-disks 152 (FIG. 4A), each of which extends about a third of the way across the diameter of the end 132. Thus, there are openings 156 wherein air can pass through to the opposite end 128 of the locking cap 16. Accordingly, when the locking cap 16 is operably secured to the syringe 10, the distal end 24 resides in the interior of the cylinder 140 and the opening 20 is sealed with the plug 148. However, even when the locking cap 16 is secured to the syringe 10, the openings 156 allow the syringe 10 to be better sterilized in that there is no enclosure within the assembled combination of the syringe body 30 and the locking cap 16 that is sealed from an ambient environment.

As discussed above, the locking cap 16 also has tabs 44 that mate with the threads 40 of the cylindrical cap fitting 36 so that the locking cap can be screwed on and off the syringe 10. The tabs 44 are attached to the outside of the cylinder 140. In the embodiment of FIGS. 4A–4D, there are two such tabs 44 that are on opposite sides of the cylinder 140 (FIG. 4A). Note, however, that alternative techniques for securing the locking cap 16 to the syringe 10 are also within the scope of the invention. For example, additional tabs 44 may be provided on the outside of the cylinder 140, or continuous threads may also be provided thereon.

To obtain arterial blood within the receptacle 54, an assembled syringe 10 with its locking cap 16 attached (this combination denoted herein a "capped syringe 160") is obtained, and may be utilized in one of two operable configurations. In a first configuration, where a patient's arterial blood pressure is sufficient to cause blood to flow unassisted into the receptacle 54, the capped syringe is used in combination with, e.g., either a needle assembly or an arterial catheter for collecting the patient's blood, but without additional attachments that could assist in drawing the patient's blood. However, when the patient's blood will not appropriately flow of its own accord into the receptacle 54, then a second configuration (shown in FIG. 3) can be provided wherein a standard 3 cc plunger type syringe 164 is used in combination with the syringe 10. In one typical embodiment, the syringe 164 has a distal end 170 with a needle attaching extension 176, a syringe body 180 having a generally cylindrical interior with a proximal end 182 and a distal end identical with distal end 170, and a plunger 188 retractable from and insertable into the interior of the syringe body 180. Accordingly, the syringe 164 has a proximal end 184 which includes the proximal end 182 of the syringe body 180 and the portion of the plunger 188 extending proximally out of the syringe body 180. As is typical of such syringes 164, the plunger 188 can be used for: (i) reducing pressure within the syringe body interior when the plunger is withdrawn from the proximal end 182, and (ii) increasing pressure within the syringe body interior when the plunger is pushed into the syringe body 180 interior from the proximal end 182. Thus, when the extension 176 is inserted into the passageway 116, the pressure of air provided between a distal end (not shown) of the plunger 188 and the distal end 170 within in the interior of syringe 164 may be communicated substantially freely across the vent 50 and into the receptacle 54.

Figure 6:
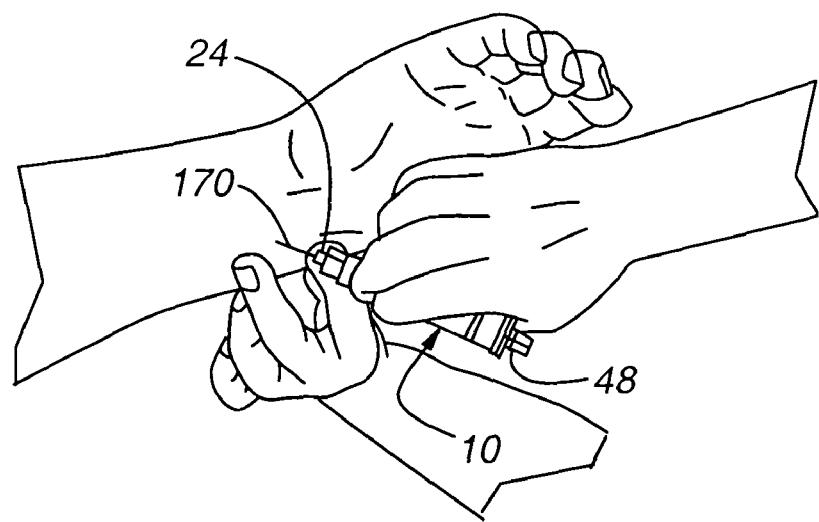
FIG. 6 shows a syringe 10 of the present invention being used to obtain a patient's blood without the assistance of the syringe 164 shown in FIG. 3.

When the present invention is used without the syringe 164 (i.e., the first configuration described above), the following steps may be performed for obtaining a sample of a patient's blood:

(a1) an assembled capped syringe 160 is obtained;
(a2) the locking cap 16 is unscrewed and detached from the syringe 10;
(a3) a hypodermic needle assembly is attached to the distal end 24 of the syringe 10 in a conventional manner;

(a4) the site for drawing a patient's blood is prepared;

(a5) the sharp end of the needle of the needle assembly is stuck into a selected artery and arterial blood is allowed to flow into the receptacle 54 until the receptacle is entirely filled with blood (FIG. 6 is illustrative of this step);

(a6) the needle is removed from the patient;

(a7) the needle assembly is detached from the syringe 10 and discarded;

(a8) typically the locking cap 16 may be reattached to the cap fitting 36 thereby sealing the receptacle 54 from air and ambient contamination (recall the vent 50 provides a seal at the proximal end 76 of the receptacle when sufficiently exposed to blood);

(a9) assuming step (a8) is performed, the capped syringe 160 may now be transported, stored and/or provided to a blood analysis instrument as desired. However, if the syringe 10 is immediately provided to an adjacent to a blood analysis instrument, it may be unnecessary to reattach the locking cap 16.

Figure 7:
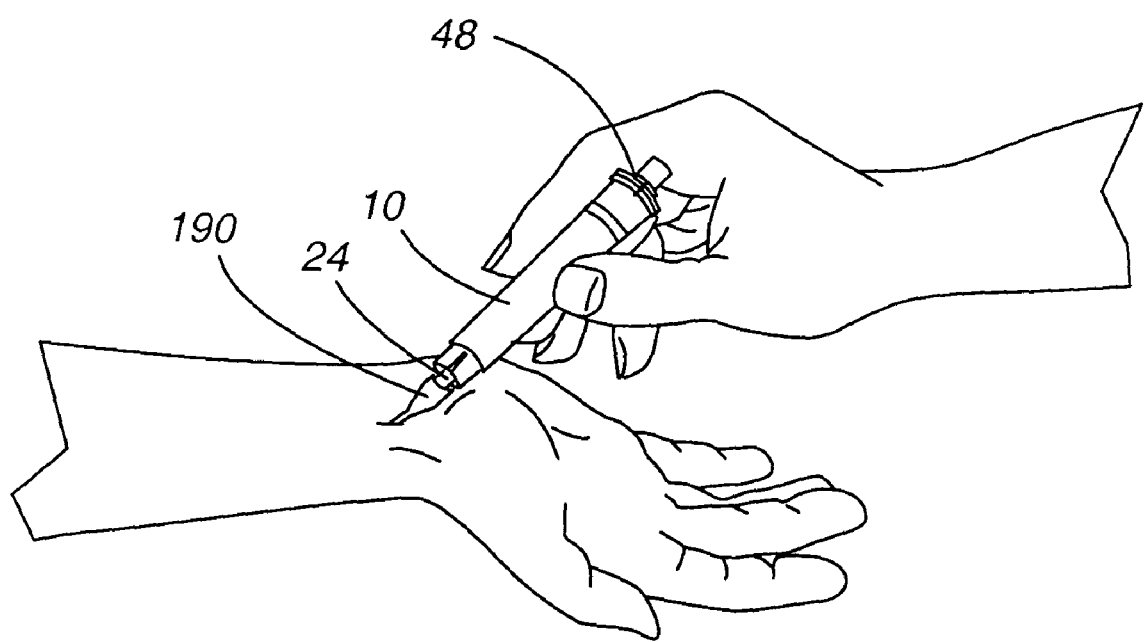
FIG. 7 shows the use of syringe 10 of the present invention for obtain a patient's blood from an intravenous catheter 190.

Referring to FIG. 7, the syringe 10 may also be used to obtain a sample of a patient's blood from an intravenous catheter 190, wherein the distal end 24 is secured to the open end of the catheter for obtaining blood therefrom. Accordingly, at least the steps (a3) through (a7) are replaced with the corresponding steps of:

(b1) the site for drawing a patient's blood is prepared (e.g., the open end of the catheter 190 is exposed;

(b2) the distal end 24 of the syringe 10 is inserted into the catheter open end for filling the receptacle 54 with blood; and (b3) once the receptacle 54 is filled, the distal end 24 of the syringe 10 is disconnected from the catheter 190 and the catheter is appropriately sealed.

When the present invention is used in combination with a syringe 164 (as in FIG. 3), steps in addition to the steps (a1) through (a9) (and/or steps (b1) through (b3)) above are performed. In particular, prior to the step (a5) or the step (b1), the following steps are performed:

(c1) a cap (not shown) that seals the opening at the end of the extension 176 is removed from the syringe 164, thereby providing air communication with the interior of the syringe body 180;

(c2) subsequently, the extension 176 is fitted into the passageway 116 of the vent cap 48 thus providing a substantially sealed air flow path between an interior of the syringe 164 and the receptacle 54;

(c3) then during step (a5) or step (b2) above, the user drawing the blood withdraws the plunger 188 from the interior of the syringe body 180 thereby reducing the air pressure in both this interior and the receptacle 54 and thus inducing the blood to more easily flow into the receptacle;

(c4) finally, following step (a7) or step (b3) above and depending upon what is to be done with the collected blood, the syringe 164 may be immediately disconnected from the syringe 10 (e.g., when the syringe 10 is to be immediately stored), or remain connected so that the syringe 164 can be used to urge the collected blood out of the receptacle 54 and, e.g., into a blood analysis instrument.

Note, that FIG. 5 is illustrative of how the syringe 10 may be provided to a blood analysis instrument 194 in either step (a9) or (b4) above. In particular, the distal end 24 of the syringe 10 may be inserted into a blood receiving orifice 200 of the instrument 194, wherein the blood within the receptacle 54 is extracted by the instrument 194. However, there are also blood analysis instruments that do not extract the blood, and accordingly the syringe 164 may be used to provide the collected blood to such a blood analysis instrument by the application of a force so that the plunger 188 retracts into the syringe body 180.

Additionally, note that blood within the receptacle 54 may be partially used, e.g., for providing to a blood analysis instrument, and a remaining portion stored in the syringe 10 (with the locking cap 16 attached thereto).

The scope of the invention also includes various alternative embodiments of the syringe 10. For instance, the vent cap 48 may also be integral with the body 30. Moreover in such an embodiment, the vent 50 may be compressibly inserted through the passageway 116 into a location whereby at least a portion of the vent expands into a volume for seating the vent within the proximal end 76 of the receptacle 54. Additionally, the ridges 56 can be provided on the exterior wall 108 of the of the receptacle 54. Accordingly, ridges on the vent cap 48 for mating or contacting the ridges on the exterior wall 108 would then be provided on the cylindrical surface of the vent cap that contacts the exterior wall 108.

The capped syringes 160 of the present invention can be readily mass produced. As mentioned above, the syringe 10 can be injection molded; however, the locking cap 16, and the vent cap 48 can also be similarly produced. The capped syringes with drawn blood might also be able to be pneumatically transported in a hospital to a location for blood analysis. Additionally, various types of vents 50 are available. Moreover, the assembly of these components to produce such capped syringes 160 is straightforward. Note, however, that prior to final packaging of the capped syringes 160, heparin or another anticoagulant is added to the receptacle 54 so that when blood is drawn into the receptacle, the blood is prevented from coagulating. The anticoagulant can be liquid or dry, such as blown powder.

In one embodiment, a plurality of such capped syringes 160 may be packaged in a single container (not shown) wherein there are there are approximately 5 to 10 of the capped syringes in a cubic inch of the container. Moreover, such capped syringes 160 need not be individually packaged or wrapped since the pathway or the blood and tip of the syringe may be assembled to ensure a tight fit and protect the sterilized areas. Thus, such a container may be sterilized (with a plurality of the capped syringes therein) and the integrity of the sterilization process remains intact due to the tight connections. Eliminating the outer package saves packaging costs, reduces overall size thereof, including shipping case, and reduces associated costs of disposal, storage, shipping and other related costs.

The foregoing discussion of the invention has been presented for purposes of illustration and description. Further, the description is not intended to limit the invention to the form disclosed herein. Consequently, variation and modification commensurate with the above teachings, within the skill and knowledge of the relevant art, are within the scope of the present invention. The embodiment described hereinabove is further intended to explain the best mode presently known of practicing the invention and to enable others skilled in the art to utilize the invention as such, or in other embodiments, and with the various modifications required by their particular application or uses of the invention.

What is claimed is:

1. A syringe, comprising:
    a syringe body that includes an outer member having a distal end and a proximal end and an inner member having a distal end, a proximal end and a receptacle for receiving blood, in a direction from said distal end to said proximal end;

a bridge integrally formed with said inner and outer members that joins said inner and outer members together; and a vent that allows air to escape and being joined to said inner member, said vent is continuously relatively more adjacent to said proximal end than said distal end of each of said inner and outer members and wherein said vent is fixed in position to define a volume in said receptacle for receiving the blood.

2. A syringe of claim 1 wherein said syringe is a first syringe and further including a second syringe joined to said first syringe for at least one of: creating negative pressure to draw blood into said first syringe and providing positive pressure to cause blood to move from said first syringe.

3. A syringe of claim 1 wherein said bridge is spaced from said distal ends of said inner and outer members.

4. A syringe of claim 1 wherein said proximal end of said inner member is substantially coterminous with said proximal end of said outer member.

5. A syringe comprising:
a syringe body that includes an outer member having a distal end and a proximal end and an inner member having a distal end and a proximal end;
a bridge integrally formed with said inner and outer members that join said inner and outer members together; and
a vent that allows air to escape and being joined to at least one of said inner and outer members, said vent is relatively more adjacent to said proximal end than said distal end of each of said inner and outer members and said bridge is relatively more adjacent to said distal ends than said proximal ends of said inner and outer members.

6. A syringe of claim 5 wherein said vent contacts said proximal end of said inner member.

7. A syringe, comprising:
a syringe body that includes an outer member having a distal end and a proximal end and an inner member having a distal end and a proximal end;
a bridge integrally formed with said inner and outer members and disposed between said proximal and distal ends thereof that joins said inner and outer members together; and
a vent that allows air to escape and being joined to at least one of said inner and outer members; and
a vent cap joined to at least one of said inner and outer members for holding said vent to said at least one of said inner and outer members.

8. A syringe of claim 7 wherein said syringe is a first syringe and further including a second syringe joined to said vent cap for controlling a flow of blood relative to said first syringe.

9. A syringe comprising:
a syringe body that includes an outer member having a distal end and a proximal end and an inner member having a distal end and a proximal end, said body distal end includes a luer lock to which a locking cap is joined;
a bridge integrally formed with said inner and outer members and disposed between said proximal and distal ends thereof that join said inner and outer members together; and
a vent that allows air to escape and being joined to at least one of said inner and outer members.

10. A method for using a first syringe, comprising:
providing a first syringe including with an outer member and an inner member;
coupling a second syringe to said first syringe, said second syringe including a plunger assembly for use in selectively producing a negative pressure and a positive pressure relative to said first syringe; and
controlling blood flow relative to said first syringe using said second syringe.

11. A method of claim 10 wherein said controlling includes causing blood to flow from said first syringe in order to test said blood.

12. A method for using a first syringe, comprising:
providing a first syringe, wherein said first syringe includes inner and outer members integrally joined together adjacent to distal ends thereof;
coupling a second syringe to said first syringe; and
controlling blood flow relative to said first syringe using a second syringe.

13. A method for using a first syringe, comprising:
providing a first syringe, wherein said first syringe has a vent joined thereto;
coupling a second syringe to said first syringe, said coupling includes joining a vent cap to a body of said first syringe adjacent said vent, said vent cap including a mating body to which said second syringe is coupled; and
controlling blood flow relative to said first syringe using said second syringe.

14. A method for sterilizing syringes, comprising:
providing a plurality of syringes including at least first and second syringes in a container, said first and second syringes being adjacent to each other and being free of any package that separates said first and second syringes from each other, wherein each of said at least first and second syringes is free of any plunger assembly used to control blood flow; and
sterilizing said plurality of syringes in said container.

15. A method of claim 14 wherein each of said at least first and second syringes has a distal end adjacent to which a distal cap is joined before said sterilizing.

16. A method for using a first syringe, comprising:
providing a first syringe;
removing a cap from said first syringe, joining a syringe needle thereto;
coupling a second syringe to said first syringe; and
using said first syringe to obtain blood while controlling blood flow relative to said first syringe using said second syringe.

17. A syringe, comprising:
a syringe body that includes an outer member having a distal end and a proximal end and an inner member having a distal end and a proximal end, said inner member defining a receptacle for collecting blood;
a bridge integrally formed with said inner and outer members that joins said inner and outer members together; and
a vent that allows air to escape while being used in preventing the escape of the blood and being joined to at least one of said inner and outer members, at least portions of said vent being located within said receptacle;
wherein said syringe is free of any plunger assembly used to control flow of the blood.

18. A method for using a first syringe, comprising:
providing a first syringe;
coupling a second syringe to said first syringe; and
controlling blood flow relative to said first syringe using said second syringe, wherein blood is received by said first syringe and said second syringe is free of any needle during said coupling and said controlling.

* * * * *